United States Patent
Martin et al.

(10) Patent No.: US 7,501,619 B2
(45) Date of Patent: Mar. 10, 2009

(54) ROTATION DEVICE FOR RADIATION SOURCE

(75) Inventors: Matthew E. Martin, Knoxville, TN (US); Ziad Burbar, Knoxville, TN (US); James Luke Corbeil, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 21 days.

(21) Appl. No.: 11/779,478

(22) Filed: Jul. 18, 2007

(65) Prior Publication Data
US 2009/0020691 A1  Jan. 22, 2009

(51) Int. Cl.
*G01D 18/00* (2006.01)
(52) U.S. Cl. .................................. 250/252.1
(58) Field of Classification Search ............... 250/252.1, 250/363.03, 363.04
See application file for complete search history.

(56) References Cited

U.S. PATENT DOCUMENTS

| | | | | |
|---|---|---|---|---|
| 4,568,097 A | * | 2/1986 | Farooq | ....................... 280/216 |
| 5,296,708 A | * | 3/1994 | Moyers et al. | ......... 250/363.03 |
| 5,990,482 A | * | 11/1999 | Bertelsen et al. | ....... 250/363.04 |
| 2003/0189174 A1 | * | 10/2003 | Tanaka et al. | .......... 250/363.03 |
| 2005/0258083 A1 | * | 11/2005 | Miller | ........................ 210/150 |

OTHER PUBLICATIONS

L. Bidaut et al., Multimodality stereotaxic correlation between XCT, PET, MRI and histology for tumoral tissue evaluation in the brain, 2004 IEEE.*
D. Schlyer et al. Preliminary studies of a simultaneous PET/MRI scanner based on the RatCAP small animal tomograph, 2006 IEEE.*

* cited by examiner

*Primary Examiner*—David P Porta
*Assistant Examiner*—Kiho Kim
(74) *Attorney, Agent, or Firm*—Peter L. Kendall

(57) ABSTRACT

A Positron Emission Tomography (PET) scanner may have a PET gantry, a calibration radiation source arranged rotatable in the PET gantry, and a drive mechanism coupled with the calibration radiation source, wherein the drive mechanism is formed by non ferromagnetic materials.

24 Claims, 3 Drawing Sheets

ROTATION DEVICE FOR RADIATION SOURCE

TECHNICAL FIELD

The present invention concerns a rotation device for a radiation source.

BACKGROUND

Magnet Resonance Imaging (MRI) is a non-invasive method using very strong magnetic fields to render images of the inside of an object and is primarily used in medical imaging to demonstrate pathological or other physiological alterations of living tissues. In addition Positron Emission Tomography (PET) is another medical imaging method, where a short-lived radioactive tracer isotope, which decays by emitting a positron, is injected usually into the blood circulation of a living subject. After the metabolically active molecule becomes concentrated in tissues of interest, the research subject or patient is placed in the imaging scanner. The molecule most commonly used for this purpose is fluorodeoxyglucose (FDG), a sugar, for which the waiting period is typically an hour.

As the radioisotope undergoes positron emission decay, it emits a positron, the antimatter counterpart of an electron. After traveling up to a few millimeters the positron encounters and annihilates with an electron, producing a pair of gamma photons moving in almost opposite directions. These are detected in the scanning device by a detector assembly, typically a scintillator material coupled to a photomultiplier, which converts the light burst in the scintillator into an electrical signal. The technique depends on simultaneous or coincident detection of the pair of photons.

Both scanning methods have their particular advantages, thus, diagnosis often requires both scanning methods. The latest complex scanning devices, thus, combine MRI and PET scanner in a way, that both devices can operate in parallel. Traditionally, normalization of a the PET scanner is performed by using an electric motor that rotates a calibration radiation source within a PET gantry. However, if an MRI and a PET scanner are combined, the strong magnetic fields of an MRI make it impossible to operate a normal electric motor. Thus, using traditional normalization methods, the PET insert camera within an MRI system must be normalized outside the MRI.

SUMMARY

According to an embodiment, a Positron Emission Tomography scanner may comprise a PET gantry, a calibration radiation source arranged rotatable in the PET gantry, and a drive mechanism coupled with the calibration radiation source, wherein the drive mechanism is formed by non ferromagnetic materials.

According to yet another embodiment, a method for calibrating a Positron Emission Tomography (PET) scanner may comprise the steps of providing a calibration radiation source arranged rotatable in a PET gantry, and rotating the calibration radiation source in the PET gantry by a drive mechanism coupled with the calibration radiation source, wherein the drive mechanism is formed by non-ferromagnetic materials.

According to yet another embodiment, a Positron Emission Tomography (PET) scanner may comprise a PET gantry, a calibration radiation source arranged rotatable in the PET gantry, and a drive mechanism coupled with the calibration radiation source, wherein the drive mechanism comprises a turbine driven by a compressed gas and a second wheel coupled with the turbine by a belt and wherein the second wheel is coupled with a support structure onto which the calibration radiation source is mounted, wherein the drive mechanism is manufactured from non-ferromagnetic material.

BRIEF DESCRIPTION OF THE DRAWINGS

A more complete understanding of the present disclosure thereof may be acquired by referring to the following description taken in conjunction with the accompanying drawings wherein.

Figure 1:
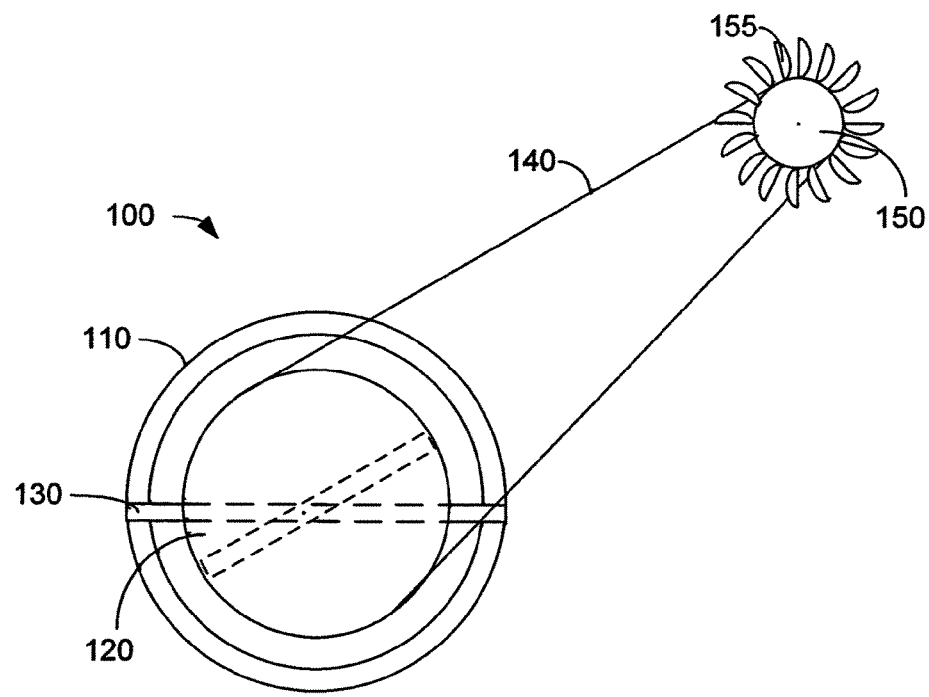
FIG. 1 shows a front view of an embodiment.

While the present disclosure is susceptible to various modifications and alternative forms, specific example embodiments thereof have been shown in the drawings and are herein described in detail. It should be understood, however, that the description herein of specific example embodiments is not intended to limit the disclosure to the particular forms disclosed herein, but on the contrary, this disclosure is to cover all modifications and equivalents as defined by the appended claims.

DETAILED DESCRIPTION

According to further enhance a PET scanner as defined above, the drive mechanism may comprises a first wheel driven by a compressed gas. Moreover, the first wheel may be coupled with a turbine driven by the compressed gas. The first wheel may comprise blades. The drive mechanism may comprise a second wheel coupled with the first wheel by a belt and the second wheel may be coupled with a support structure onto which the calibration radiation source can be mounted. The drive mechanism may be manufactured from plastic material. The drive mechanism may be manufactured from at least one plastic material selected from the group consisting of polyethylene, polypropylene, and Acrylonitrile butadiene styrene (ABS). The support structure can be a sprocket gear coupled with the second wheel via a gear mechanism. The first and second wheels may be sprocket gears and the belt may be a toothed belt. The PET scanner may further comprise a control device for controlling a gas flow driving the first wheel. The PET gantry may comprise mounting holes and the drive mechanism can be mounted using plastic mounting strut bolts in the mounting holes. The PET scanner can be arranged within an Magnetic Resonance Imaging (MRI) system. The drive mechanism may comprise a turbine driven by a hydraulic fluid. The drive mechanism may comprise a flexible drive shaft manufactured from non ferromagnetic materials.

According to another enhancement, the method as defined above may furthermore comprise the step of driving the drive mechanism by a compressed gas. The method may also comprise the step of driving a turbine coupled with a first wheel. The compressed gas can be compressed air. The drive mechanism may be manufactured from plastic material. The drive mechanism can be manufactured from at least one plastic material selected from the group consisting of polyethylene, polypropylene, and Acrylonitrile butadiene styrene (ABS). The method may also further comprise the step of driving the drive mechanism by a hydraulic fluid. The method may also comprise the step of driving the drive mechanism by a flexible drive shaft manufactured from non ferromagnetic materials.

Figure 2:
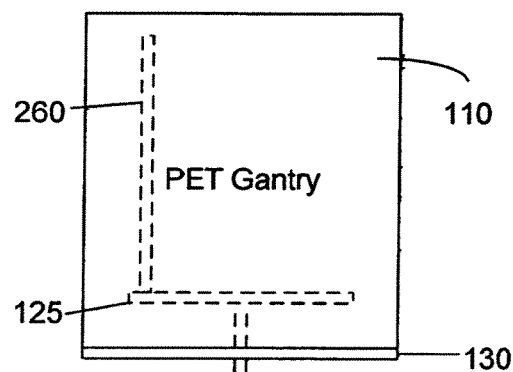
FIG. 2 shows a top view of the embodiment shown in FIG. 1.
Figure 2:
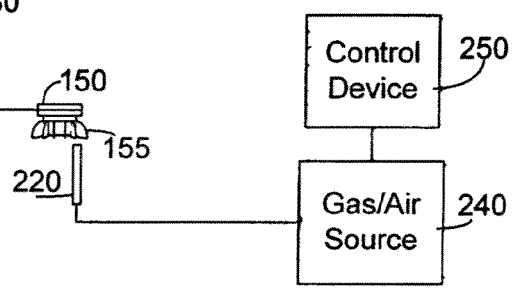
Figure 3:
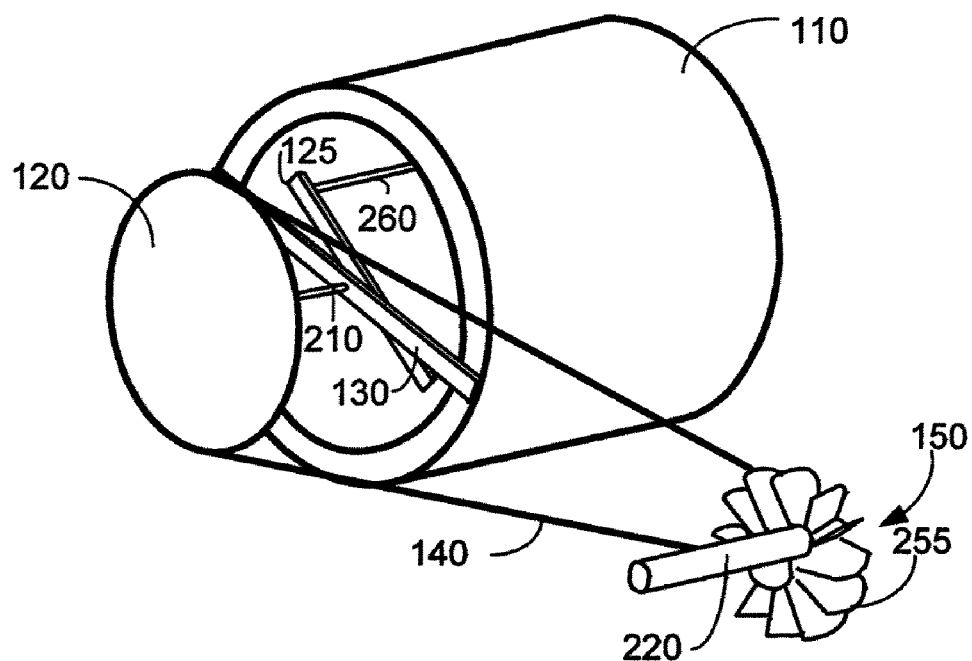
FIG. 3 shows a perspective view of a first embodiment as shown in FIG. 1.

FIGS. 1, 2 and 3 show an embodiment of drive mechanism 100 for a PET scanner that can be integrated with an MRI system in a front and top view. The PET scanner comprises a PET gantry 110 onto which a first drive wheel 120 is mounted, for example, by a support structure 130. The first drive wheel is coupled with another support structure 125 via a shaft 210. This support structure 125 can be, for example, a rotating arm 125 which extends from the axis of the shaft in one direction. Alternatively, the support structure may extend in opposite directions from the shaft axis. Support structure 125 carries the radiation source on one end of an arm. Depending on the size and form of the radiation source, other support structures may be used. By turning drive wheel 120, the radiation source 260 rotates within the PET gantry 110 according to respective calibration procedure.

The first drive wheel 120 may be coupled to second drive wheel 150 via a coupling belt 140. According to one embodiment, drive wheels 120 and 150 are each in the form of gears such as sprockets and the drive belt 140 may be a toothed belt. However, if applicable, the drive system also may be embodied by grooved wheels and a rubber belt as used for example in belt driven turntables.

The second drive wheel may be equipped with a plurality of blades 155 or coupled with a turbine 255. In front of this turbine 255 or the blades 155, the outlet of a gas supply rod or hose is placed to deliver a stream of gas to the blades 155 or turbine 255 in such a way that depending on the gas pressure delivered from tube 220, the second drive wheel rotates more or less in the designated direction. To this end, tube 220 is coupled with a gas/air source 240 that delivers air/gas in a controlled fashion. Tube 220 may have a nozzle attached to its proximate end to deliver air/gas at a higher flow rate. The gas/air source may be a gas/air supply tank having a controllable outlet valve controlled by a respective control device 250. Alternatively, air or any other suitable gas may be delivered by a respective plumbing structure and the gas/air source may be a controllable valve controlled by device 250 to deliver the required gas to drive turbine 255 and its coupled drive wheel 150.

FIG. 3 is a perspective view of an embodiment according to FIGS. 1 and 2. As can be seen, when flow rate regulated compressed air or other suitable gas exits the tube 220, the out coming air/gas hits the blades of turbine 255 which will rotate accordingly. Through belt 140 drive wheel 120 is rotated and, thus, via shaft 210 and support structure 125, the radiation source 260 within PET gantry 110 as required for a respective calibration process.

Figure 4:
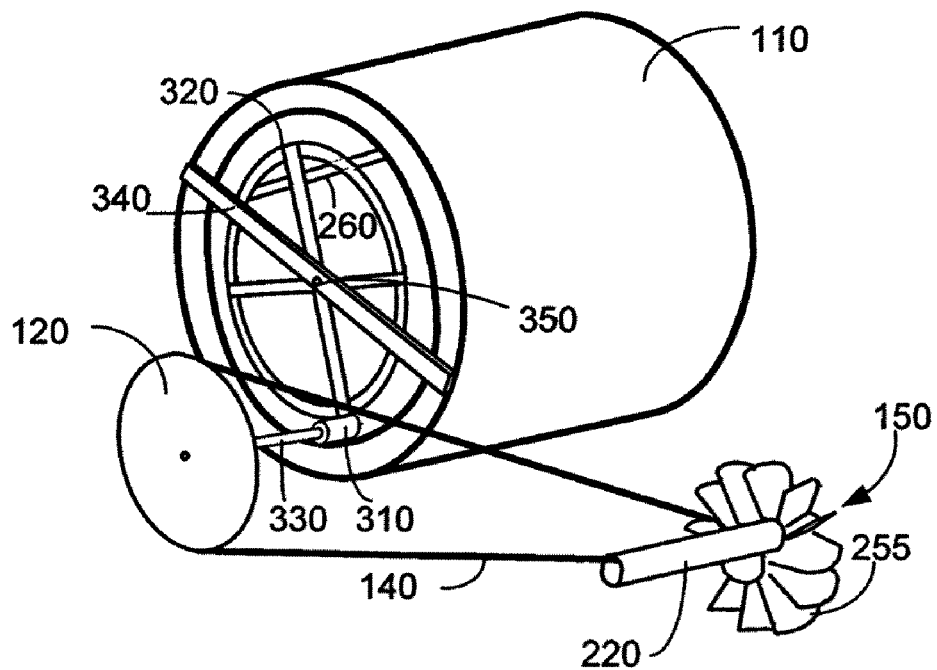
FIG. 4 shows a perspective view of a second embodiment.

FIG. 4 shows a different embodiment of the drive system. Again, a primary drive wheel 150 and a secondary drive wheel 120 are used. However, the secondary drive wheel 120 drives a small sprocket 310 via shaft 330. This small sprocket 310 engages in outer toothed area of a sprocket 320 arranged within the PET gantry 110. Sprocket 320 is mounted within the PET gantry 110 via a support structure 340 and shaft 350 which can be similar to structure 130 and shaft 210. The radiation source 260 can be directly mounted on sprocket 320 in this embodiment. This embodiment allows for a more flexible adjustment of the gear ratio of the entire arrangement by adjustment of the respective sizes of the used gears and sprockets.

All elements of the arrangement shown to drive the radiation source can be manufactured from non ferromagnetic materials. For example, the turbine can be manufactured polyethylene, prolypropylene, Acrylonitrile butadiene styrene (ABS), or other suitable materials. Similarly all wheels, sprocket gears, the belt, etc. can be manufactured from similar materials.

As shown in FIGS. 3 and 4, during calibration of a PET scanner, the radiation source 260 is rotated around the central axis of the PET gantry. This radiation source 260 emits a high energy radiation that is collected by the PET cameras by rotating the radiation source 260 through the shown mechanism according to the different embodiments, a uniform distribution of radiation is collected. The arrangement as shown in the figures will not be affected by the strong magnetic fields because all parts can be manufactured from non-ferromagnetic material. As shown in the Figures, regulated compressed air/gas is forced over the plastic turbine 255 which is connected to the small sprocket gear 150. As the regulated air/gas flows across the turbine at a known flow rate, the small sprocket gear 150 turns in direct proportion the turbine 155/255 as seen by equation 1:

$$V_{sprocket1} = V_{turbine} \tag{1}$$

where $V_{sprocket1}$=the angular speed of sprocket 150, and $V_{turbine}$=the angular speed of the turbine 255 controlled directly by the flow rate of the compressed air/gas.

The speed of the larger sprocket 120 is directly related to the speed of sprocket 150 by the following relationship:

$$V_{sprocket1} * D_{sprocket1} = V_{sprocket2} * D_{sprocket2} \tag{2}$$

where $D_{sprocket1}$=the diameter of sprocket 150, and $D_{sprocket2}$=the diameter of sprocket 120.

A plastic mounting strut 130 is used in the shown embodiments that bolts into the PET gantry 110 using existing holes. A ceramic rod can be used as shaft 210 that is rigidly attached to sprocket 120 and may lead through the mounting bracket 130 using a Teflon bearing. This ceramic rod 210 is rigidly attached to the plastic arm 125 that holds the radiation source. In this way, precise control of the angular velocity of the radiation source 260 can be achieved by simply regulating the compressed air/gas and modifying the diameters of the two sprockets 120 and 150.

Figure 5:
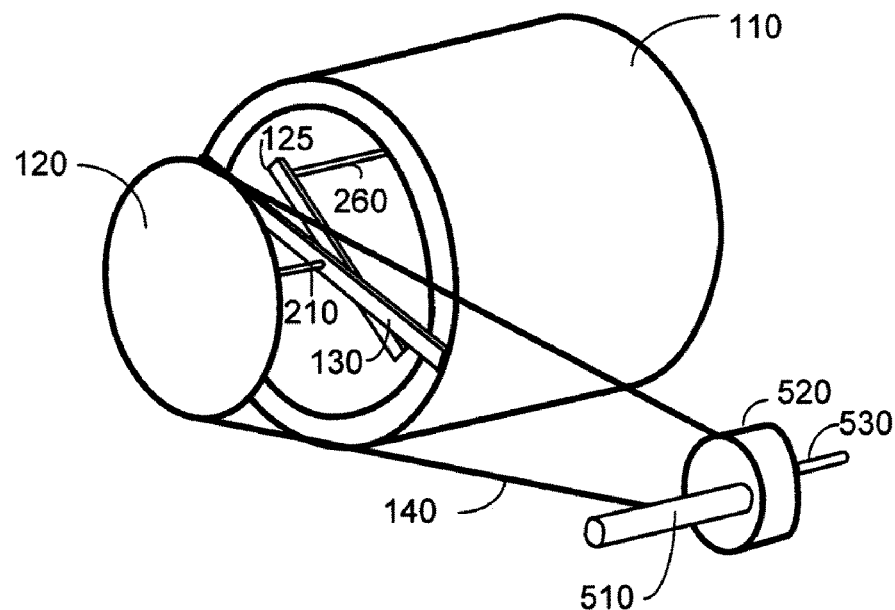
FIG. 5 shows a perspective view of a third embodiment.

FIG. 5 shows yet another embodiment. In this embodiment a hydraulic fluid is used to drive a turbine instead of gas as disclosed in the above embodiments. According to this embodiment, a turbine is arranged within a housing 520. An input connection 510 may be connected to a fluid source such as a hydraulic tank (not shown). An output connection 530 is also provided to which a respective hydraulic control loop may be connected. The turbine 520 may comprise an drive sprocket coupled with the inner hydraulic turbine to drive belt 140. Thus, a known hydraulic control circuit may be connected to this drive arrangement.

Figure 6:
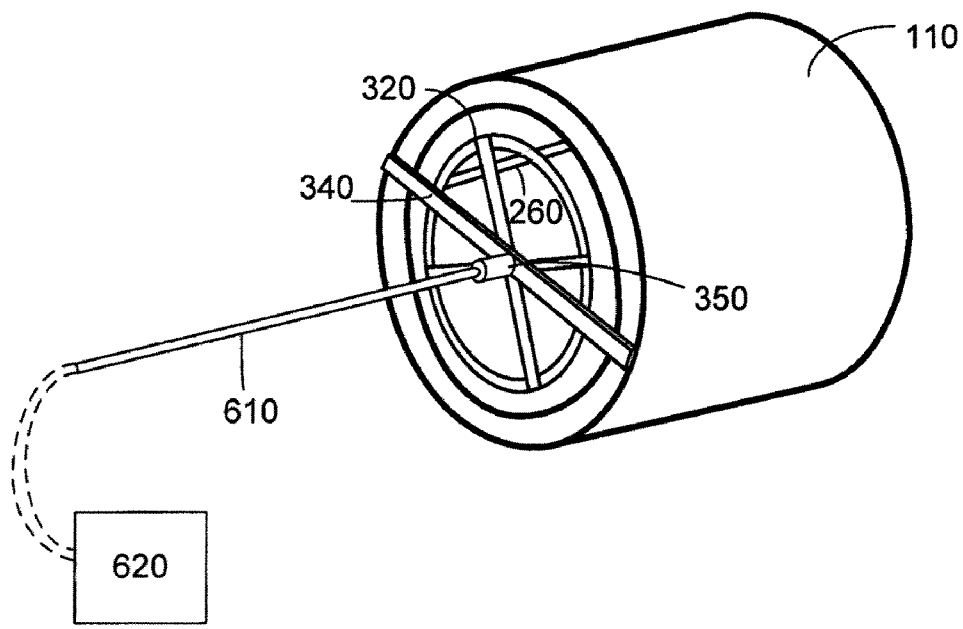
FIG. 6 shows a perspective view of a fourth embodiment.

FIG. 6 shows yet another embodiment in which a long flexible drive shaft 610 is coupled to an AC or DC motor 620 that is located at a considerable distance from the magnetic field allowing the motor to function properly. The broken lines indicate that the flexible coupling may be arranged at a considerable distance.

While embodiments of this disclosure have been depicted, described, and are defined by reference to example embodiments of the disclosure, such references do not imply a limitation on the disclosure, and no such limitation is to be inferred. The subject matter disclosed is capable of considerable modification, alteration, and equivalents in form and function, as will occur to those ordinarily skilled in the pertinent art and having the benefit of this disclosure. The depicted and described embodiments of this disclosure are examples only, and are not exhaustive of the scope of the disclosure.

What is claimed is:

1. A Positron Emission Tomography (PET) scanner comprising: a PET gantry, the gantry comprising a calibration radiation source; and
   a rotatable drive mechanism, formed by non ferromagnetic materials, mechanically connected to the radiation source;
   wherein the drive mechanism is configured to rotate the radiation source.

2. The PET scanner according to claim 1, wherein the drive mechanism comprises a first wheel driven by a compressed gas.

3. The PET scanner according to claim 2, wherein the first wheel is coupled with a turbine driven by said compressed gas.

4. The PET scanner according to claim 2, wherein the first wheel comprises blades.

5. The PET scanner according to claim 2, wherein the drive mechanism comprises a second wheel coupled with said first wheel by a belt and wherein the second wheel is coupled with a support structure onto which said calibration radiation source is mounted.

6. The PET scanner according to claim 5, wherein the support structure comprises a sprocket gear coupled with said second wheel via a gear mechanism.

7. The PET scanner according to claim 5, wherein the first and second wheels are sprocket gears and the belt is a toothed belt.

8. The PET scanner according to claim 2, further comprising a control device for controlling a gas flow driving said first wheel.

9. The PET scanner according to claim 1, wherein the drive mechanism is manufactured from plastic material.

10. The PET scanner according to claim 1, wherein the drive mechanism is manufactured from at least one plastic material selected from the group consisting of polyethylene, polypropylene, and Acrylonitrile butadiene styrene (ABS).

11. The PET scanner according to claim 1, wherein the PET gantry comprises mounting holes and the drive mechanism is mounted using plastic mounting strut bolts in said mounting holes.

12. The PET scanner according to claim 1, wherein the PET scanner is arranged within an Magnetic Resonance Imaging (MRI) system.

13. The PET scanner according to claim 1, wherein the drive mechanism comprises a turbine driven by a hydraulic fluid.

14. The PET scanner according to claim 1, wherein the drive mechanism comprises a flexible drive shaft manufactured from non ferromagnetic materials.

15. A method for calibrating a Positron Emission Tomography (PET) scanner comprising the steps of:
   providing a calibration radiation source arranged rotatable in a PET gantry;
   mechanically connecting the radiation source to a drive mechanism consisting of non-ferromagnetic materials; and
   rotating the radiation source by the drive mechanism.

16. The method according to claim 15, wherein the step of rotating comprises applying compressed gas to the drive mechanism.

17. The method according to claim 16, wherein the step of rotating further comprises driving a turbine coupled with a first wheel.

18. The method according to claim 15, wherein the compressed gas comprises compressed air.

19. The method according to claim 15, wherein the drive mechanism comprises plastic material.

20. The method according to claim 15, wherein the drive mechanism is manufactured from at least one plastic material selected from the group consisting of polyethylene, polypropylene, and Acrylonitrile butadiene styrene (ABS).

21. The method according to claim 15, wherein the step of rotating comprises applying hydraulic fluid to the drive mechanism.

22. The method according to claim 15, wherein the step of rotating comprises driving said drive mechanism by a flexible drive shaft manufactured from non ferromagnetic materials.

23. A Positron Emission Tomography (PET) scanner comprising:
   a PET gantry;
   a calibration radiation source arranged rotatable in said PET gantry;
   a drive mechanism mechanically connected to said calibration radiation source, wherein the drive mechanism comprises a turbine driven by a compressed gas and a second wheel coupled with said turbine by a belt and wherein the second wheel is coupled with a support structure onto which said calibration radiation source is mounted, wherein the drive mechanism is manufactured from non-ferromagnetic material.

24. The PET scanner according to claim 23, wherein the PET scanner is arranged within an Magnetic Resonance Imaging (MRI) system.

* * * * *